US009642604B2

(12) United States Patent
Phillips

(10) Patent No.: US 9,642,604 B2
(45) Date of Patent: May 9, 2017

(54) HEMOSTATIC SYSTEM AND ITS METHODS OF USE

(75) Inventor: Victor Matthew Phillips, Jefferson City, MO (US)

(73) Assignee: Phillips Medical LLC, Jefferson City, MO (US)

( * ) Notice: Subject to any disclaimer, the term of this patent is extended or adjusted under 35 U.S.C. 154(b) by 740 days.

(21) Appl. No.: 13/445,510

(22) Filed: Apr. 12, 2012

(65) Prior Publication Data

US 2013/0274708 A1 Oct. 17, 2013

(51) Int. Cl.

| | |
|---|---|
| ***A61B 17/08*** | (2006.01) |
| ***A61B 17/00*** | (2006.01) |
| *A61B 90/00* | (2016.01) |

(52) U.S. Cl.

CPC .. *A61B 17/0057* (2013.01); *A61B 2017/0065* (2013.01); *A61B 2090/062* (2016.02)

(58) Field of Classification Search

CPC .......... A61B 2019/462; A61B 17/0057; A61B 2017/0065

USPC ..... 606/214, 213; 604/93.01, 103.01, 168.01

See application file for complete search history.

(56) References Cited

U.S. PATENT DOCUMENTS

| | | | | |
|---|---|---|---|---|
| 4,738,658 | A | | 4/1988 | Magro et al. |
| 4,850,960 | A | | 7/1989 | Grayzel |
| 4,890,612 | A | | 1/1990 | Kensey |
| 4,895,564 | A | | 1/1990 | Farrell |
| 4,929,246 | A | | 5/1990 | Sinofsky |
| 5,061,274 | A | | 10/1991 | Kensey |
| 5,108,421 | A | | 4/1992 | Fowler |
| 5,222,974 | A | | 6/1993 | Kensey et al. |
| 5,282,827 | A | | 2/1994 | Kensey et al. |
| 5,290,310 | A | * | 3/1994 | Makower et al. ............ 606/213 |
| 5,306,254 | A | | 4/1994 | Nash et al. |
| 5,326,350 | A | | 7/1994 | Li |
| RE34,866 | E | | 2/1995 | Kensey et al. |
| 5,391,183 | A | | 2/1995 | Janzen et al. |
| 5,415,657 | A | | 5/1995 | Taymor-Luria |
| 5,431,639 | A | | 7/1995 | Shaw |
| 5,437,292 | A | | 8/1995 | Kipshidze et al. |
| 5,437,631 | A | * | 8/1995 | Janzen .......................... 604/506 |
| 5,441,517 | A | | 8/1995 | Kensey et al. |

(Continued)

OTHER PUBLICATIONS

International Search Report and Written Opinion of PCT/US2011/032490; Jun. 29, 2011; 10 pages.

(Continued)

*Primary Examiner* — Gregory Anderson
*Assistant Examiner* — Sarah Simpson
(74) *Attorney, Agent, or Firm* — Armstrong Teasdale LLP

(57) ABSTRACT

A hemostatic system includes an inner tube and an injection sheath coupled to the inner tube. The injection sheath houses at least a section of the inner tube. The inner tube defines a first lumen configured to channel a fluid therethrough, and the injection sheath defines a second lumen configured to channel a hemocoagulant agent therethrough. An injection device is positionable within the injection sheath to facilitate channeling the hemocoagulant agent through the second lumen. The injection device defines a third lumen in fluid communication with the first lumen when the injection device is positioned within the injection sheath. The injection device includes a valve that is moveable to selectively restrict access to a portion of the injection device.

18 Claims, 6 Drawing Sheets

(56) References Cited

U.S. PATENT DOCUMENTS 5,443,481 A 8/1995 Lee
5,591,204 A 1/1997 Janzen et al.
5,645,566 A 7/1997 Brenneman et al.
5,649,959 A * 7/1997 Hannam ............ A61B 17/0057 604/181
5,653,730 A 8/1997 Hammerslag
5,665,107 A 9/1997 Hammerslag
5,676,689 A 10/1997 Kensey et al.
5,707,393 A 1/1998 Kensey et al.
5,716,375 A 2/1998 Fowler
5,725,498 A 3/1998 Janzen et al.
5,741,223 A 4/1998 Janzen et al.
5,766,157 A 6/1998 Tilton, Jr.
5,766,206 A 6/1998 Wijkamp et al.
5,782,861 A 7/1998 Cragg et al.
5,830,130 A * 11/1998 Janzen et al. ................. 606/213
5,843,124 A 12/1998 Hammerslag
5,868,762 A 2/1999 Cragg et al.
5,928,266 A * 7/1999 Kontos ......................... 606/213
5,935,147 A 8/1999 Kensey et al.
5,951,583 A 9/1999 Jensen et al.
5,984,950 A 11/1999 Cragg et al.
6,045,570 A 4/2000 Epstein et al.
6,056,768 A 5/2000 Cates et al.
6,071,301 A * 6/2000 Cragg ................ A61B 17/0057 604/265
6,090,130 A 7/2000 Nash et al.
6,296,657 B1 10/2001 Brucker
6,302,898 B1 * 10/2001 Edwards et al. .............. 606/214
6,315,753 B1 11/2001 Cragg et al.
6,325,789 B1 12/2001 Janzen et al.
6,371,974 B1 4/2002 Brenneman et al.
6,371,975 B2 4/2002 Cruise et al.
6,527,734 B2 3/2003 Cragg et al.
6,544,236 B1 4/2003 Cragg et al.
6,547,806 B1 4/2003 Ding
6,610,026 B2 8/2003 Cragg et al.
6,676,664 B1 1/2004 Al-Assir
6,743,248 B2 6/2004 Edwards et al.
6,830,756 B2 12/2004 Hnojewyj
6,863,680 B2 3/2005 Ashby
6,984,219 B2 1/2006 Ashby et al.
7,029,489 B1 4/2006 Ashby et al.
7,037,322 B1 5/2006 Sing et al.
7,048,710 B1 5/2006 Cragg et al.
7,201,725 B1 4/2007 Cragg et al.
7,318,933 B2 1/2008 Hnojewyj
7,335,219 B1 2/2008 Ashby et al.
7,455,680 B1 11/2008 Ashby et al.
7,611,479 B2 * 11/2009 Cragg et al. .................... 604/13
7,625,352 B1 12/2009 Ashby et al.
8,845,580 B2 9/2014 Gellman
2001/0018598 A1 8/2001 Cruise et al.
2003/0009194 A1 1/2003 Saker et al.
2003/0088271 A1 5/2003 Cragg et al.
2003/0093116 A1 5/2003 Nowakowski
2003/0100921 A1 5/2003 Addis et al.
2004/0019328 A1 1/2004 Sing et al.
2004/0098024 A1 5/2004 Dieck et al.
2004/0102730 A1 5/2004 Davis et al.
2004/0193170 A1 9/2004 Kemppainen et al.
2006/0100664 A1 5/2006 Pai et al.
2007/0038245 A1 2/2007 Morris et al.
2007/0123816 A1 5/2007 Zhu et al.
2008/0038313 A1 2/2008 Addis et al.
2008/0046005 A1 2/2008 Lenker et al.
2008/0071310 A1 3/2008 Hoffman et al.
2008/0082122 A1 4/2008 Khosravi et al.
2008/0161849 A1 7/2008 Cates et al.
2009/0088793 A1 4/2009 Bagaoisan et al.
2009/0137965 A1 5/2009 Kim et al.
2009/0143808 A1 6/2009 Houser
2009/0171282 A1 7/2009 Pipenhagen et al.
2009/0275916 A1 11/2009 Harms et al.
2010/0249720 A1 9/2010 Biyani et al.
2011/0106064 A1 5/2011 Zou et al.
2011/0137338 A1 * 6/2011 Phillips ......................... 606/213
2011/0282381 A1 11/2011 Cronin et al.
2014/0135824 A1 5/2014 Terwey et al.

OTHER PUBLICATIONS

International Search Report and Written Opinion of PCT/US2013/034799, dated Jun. 13, 2013, pp. 23.

* cited by examiner

HEMOSTATIC SYSTEM AND ITS METHODS OF USE

BACKGROUND OF THE INVENTION

The subject matter described herein relates generally to medical devices and, more particularly, to a hemostatic system.

Catheter introducers are known to provide access to an artery for at least some medical procedures including, without limitation, cardiac catheterizations and peripheral endovascular procedures. After conducting such medical procedures, the catheter introducer is removed from the access site, leaving an arterial opening. At least some body fluids including, without limitation, blood are discharged from the arterial opening. Excess blood loss may endanger and/or traumatize the patient. One known method of controlling blood loss is through direct manual pressure over the arterial opening.

BRIEF SUMMARY OF THE INVENTION

In one aspect, a method is provided for sealing a puncture of a vessel. The method includes housing at least a section of an inner tube within an injection sheath. An injection device is positioned within the injection sheath such that the injection device houses at least the section of the inner tube. A first lumen is defined by an inner surface of the inner tube, a second lumen is defined by an inner surface of the injection sheath and an outer surface of the inner tube, and a third lumen is defined by an inner surface of the injection device. The third lumen is in fluid communication with the first lumen. The inner tube is advanced until a fluid is channeled through the first lumen and the third lumen. A valve is moved to selectively restrict the fluid from being discharged from the third lumen. The injection device is advanced through the injection sheath to channel a hemocoagulant agent through the second lumen.

In another aspect, a hemostatic system is provided for sealing a puncture of a vessel. The hemostatic system includes an inner tube and an injection sheath coupled to the inner tube. The injection sheath houses at least a section of the inner tube. The inner tube defines a first lumen configured to channel a fluid therethrough, and the injection sheath defines a second lumen configured to channel a hemocoagulant agent therethrough. An injection device is positionable within the injection sheath to facilitate channeling the hemocoagulant agent through the second lumen. The injection device defines a third lumen in fluid communication with the first lumen when the injection device is positioned within the injection sheath. The injection device includes a valve that is moveable to selectively restrict access to a portion of the injection device.

In yet another aspect, a hemostatic system is provided for sealing a puncture of a vessel. The hemostatic system includes an inner tube defining an inner tube lumen configured to channel a fluid therethrough. An outer tube is removably coupled to the inner tube. The outer tube defines an outer tube lumen in fluid communication with the inner tube lumen such that the outer tube lumen is configured to channel the fluid therethrough. The outer tube includes a valve that is moveable to selectively restrict access to a portion of said outer tube. An injection sheath is sized to house at least a section of the inner tube. The injection sheath defines an injection sheath lumen configured to channel a hemocoagulant agent therethrough.

The features, functions, and advantages described herein may be achieved independently in various embodiments of the present disclosure or may be combined in yet other embodiments, further details of which may be seen with reference to the following description and drawings.

DETAILED DESCRIPTION OF THE INVENTION

The methods and apparatus described herein relate to medical devices and, more particularly, to a hemostatic system. The hemostatic system described herein facilitates sealing an opening of a blood vessel. More particularly, in at least one embodiment, the hemostatic system includes an inner tube and an injection sheath coupled to the inner tube. An outer tube or injection device is coupled to the inner tube. The injection device is advanced through the injection sheath to discharge a hemocoagulant agent from the injection sheath adjacent the opening. The hemocoagulant agent seals the opening to reduce a time required for hemostasis and/or ambulation.

As used herein, an element or step recited in the singular and preceeded with the word “a” or “an” should be understood as not excluding plural said elements or steps, unless such exclusion is explicitly stated. Further, references to “one embodiment” are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional such elements not having that property.

Figure 1:
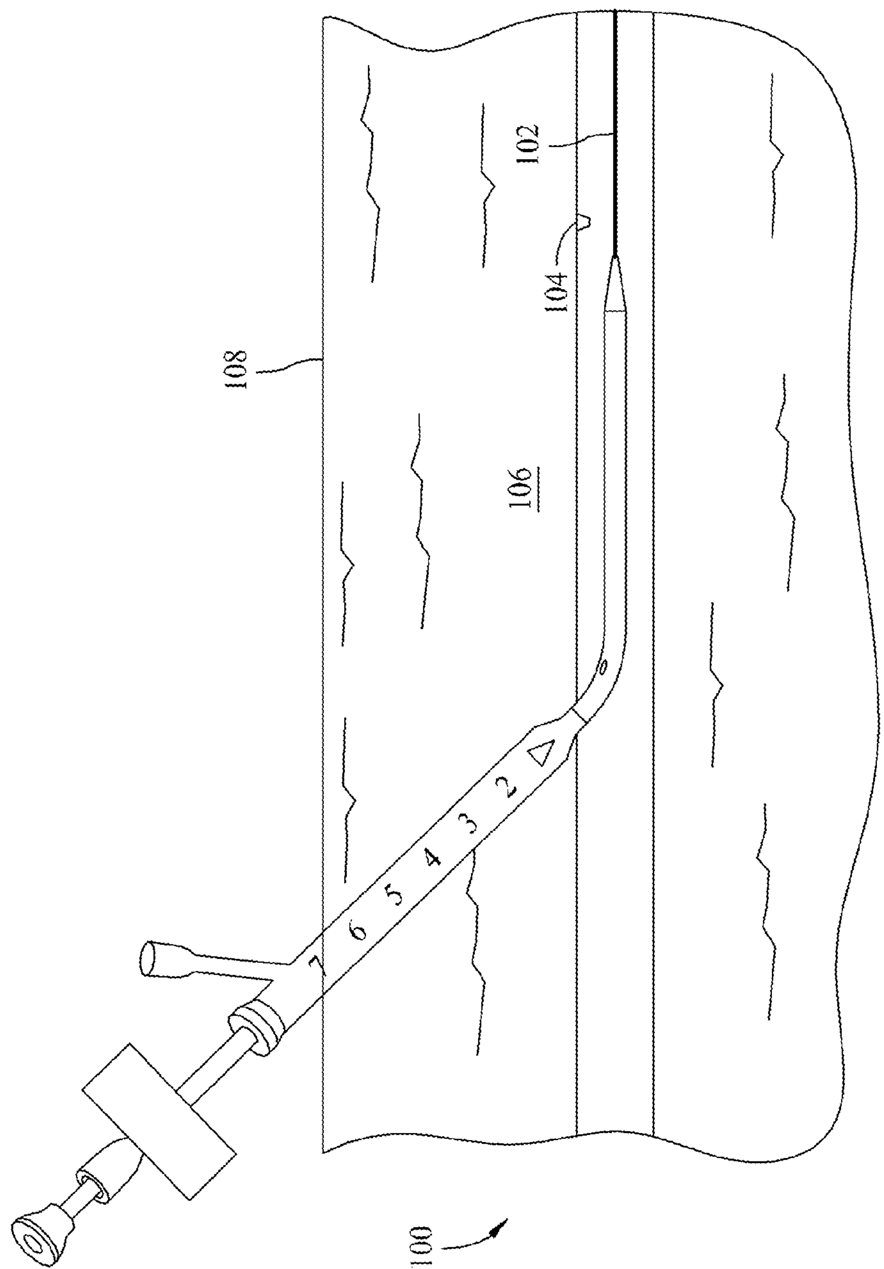
FIG. 1 is a partial cross-sectional view of an access site including an exemplary hemostatic system.

FIG. 1 is a partial cross-sectional view of an access site including an exemplary hemostatic system 100, a guidewire 102, and a vessel or, more particularly, an artery 104 within subcutaneous tissue 106 under a skin surface 108.

Figure 2:
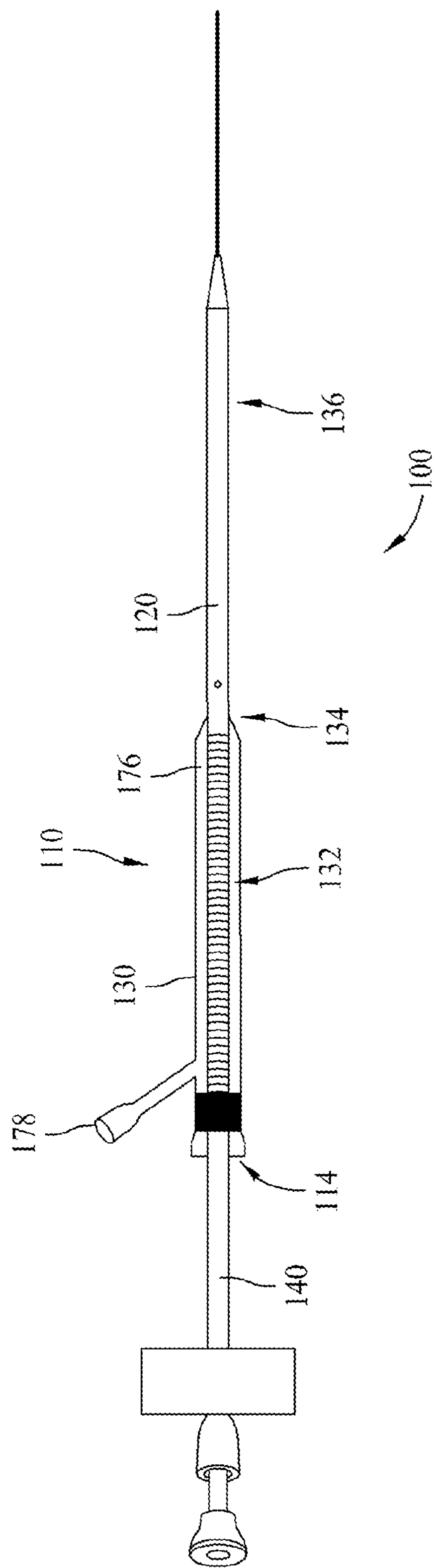
FIG. 2 is a partial cross-sectional view of the hemostatic system shown in FIG. 1.

FIG. 2 is a partial cross-sectional view of hemostatic system 100. In the exemplary embodiment, hemostatic system 100 includes a locator device 110 having a distal end 112 and a proximal end 114. In the exemplary embodiment, hemostatic system 100 includes an inner tube 120 and an injection sheath 130 housing a proximal section 132 of inner tube 120. More specifically, in the exemplary embodiment, injection sheath 130 is coupled to a midsection 134 of inner tube 120 such that a distal section 136 of inner tube 120 is generally exposed. That is, in the exemplary embodiment, injection sheath 130 does not house distal section 136 of inner tube 120. Moreover, in the exemplary embodiment, hemostatic system 100 includes an outer tube or injection device 140 that is positionable and/or moveable within injection sheath 130.

Figure 3:
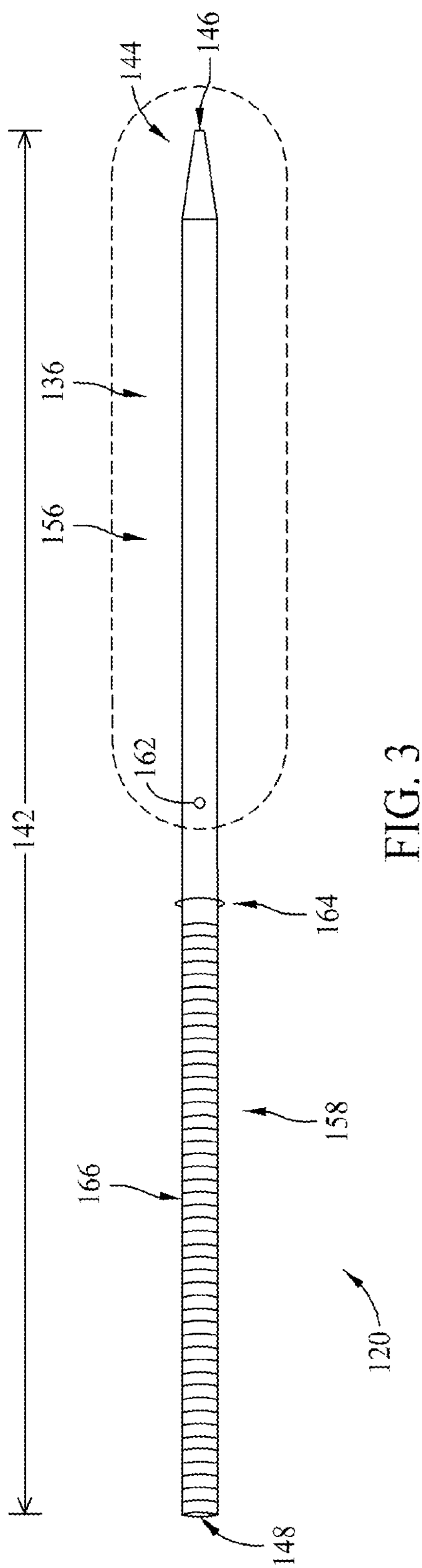
FIG. 3 is a perspective view of an exemplary inner tube that may be used with the hemostatic system shown in FIG. 1.
Figure 4:
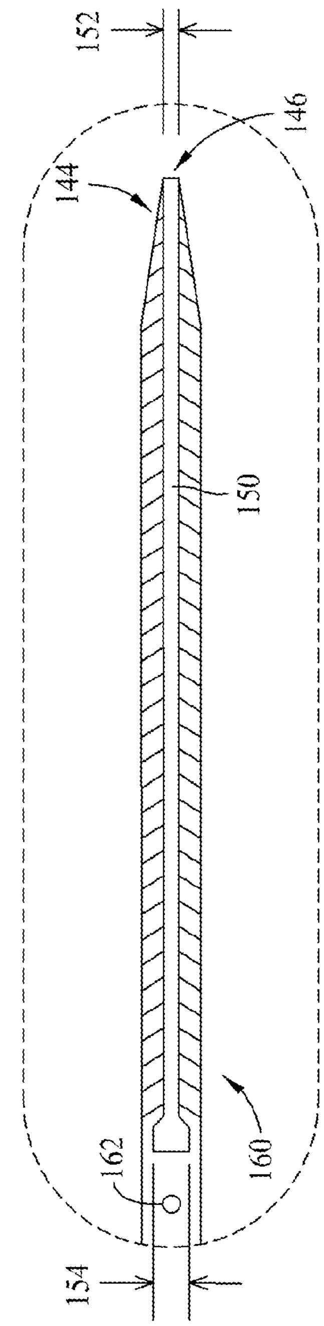
FIG. 4 is a cut-away view of the inner tube shown in FIG. 3.

FIG. 3 is a perspective view of inner tube 120. FIG. 4 is a cut-away view of inner tube 120. In the exemplary embodiment, inner tube 120 has a length 142 of at least approximately 10 centimeters (cm) (3.94 inches (in.)). More particularly, in the exemplary embodiment, length 142 is between approximately 15 cm (5.91 in.) and approximately 20 cm (7.87 in.). Alternatively, inner tube 120 may have any length that enables hemostatic system 100 to function as described herein. In the exemplary embodiment, a distal end 144 of inner tube 120 is tapered to facilitate traversing distal section 136 under skin surface 108 through subcutaneous tissue 106 and into the lumen of artery 104.

In the exemplary embodiment, inner tube 120 includes a distal end opening 146, a proximal end opening 148, and a first lumen 150 (shown in FIG. 4) defined therebetween. In the exemplary embodiment, distal end opening 146 has a first inner diameter 152 (shown in FIG. 4), and proximal end opening 148 has a second inner diameter 154 that is different from first inner diameter 152. More specifically, in the exemplary embodiment, first inner diameter 152 is substantially equal to an outer diameter of guidewire 102, and second inner diameter 154 is larger than first inner diameter 152 to channel a fluid through first lumen 150 about guidewire 102. For example, in the exemplary embodiment, first inner diameter 152 is approximately 0.035 in. to receive a 0.035 in. guidewire, and second inner diameter 154 is larger than 0.035 in. Alternatively, inner diameters 152 and/or 154 may be any size, shape, and/or configuration that enables inner tube 120 to function as described herein.

Accordingly, in the exemplary embodiment, first lumen 150 includes a first portion 156 corresponding to first inner diameter 152, and a second portion 158 corresponding to second inner diameter 154. More specifically, in the exemplary embodiment, first portion 156 extends between distal end opening 146 and a location 160 approximately 6 cm (2.36 in.) from distal end opening 146, and second portion 158 extends between proximal end opening 148 and location 160. Alternatively, portions 156 and/or 158 may have any size, shape, and/or configuration that enables inner tube 120 to function as described herein.

In the exemplary embodiment, inner tube 120 includes a side opening 162 that is in fluid communication with first lumen 150. In the exemplary embodiment, side opening 162 is disposed approximately 7 cm (2.76 in.) from distal end opening 146. More specifically, in the exemplary embodiment, side opening 162 is in fluid communication with second portion 158 of first lumen 150. Alternatively, side opening 162 may be disposed in any location that enables inner tube 120 to function as described herein.

In the exemplary embodiment, inner tube 120 includes a first coupling mechanism 164 configured to couple inner tube 120 to injection sheath 130. For example, in the exemplary embodiment, first coupling mechanism 164 is a circumferential ridge that is configured to engage an inner surface of injection sheath 130 in a snap-fit configuration. Alternatively, first coupling mechanism 164 may have any configuration that enables inner tube 120 to be coupled to injection sheath 130. For example, in at least some embodiments, inner tube 120 may be integrally formed with injection sheath 130 such that they form a unitary component. In the exemplary embodiment, first coupling mechanism 164 is disposed at midsection 134 of inner tube 120 approximately 8 cm (3.15 in.) from distal end opening 146. Accordingly, in the exemplary embodiment, side opening 162 is generally exposed when injection sheath 130 is coupled to inner tube 120.

Moreover, in the exemplary embodiment, inner tube 120 includes a second coupling mechanism 166 configured to couple inner tube 120 to injection device 140. For example, in the exemplary embodiment, second coupling mechanism 166 is a plurality of threads that are configured to engage an inner surface of injection device 140 in a threaded configuration. Alternatively, second coupling mechanism 166 may have any configuration that enables hemostatic system 100 to function as described herein. In the exemplary embodiment, second coupling mechanism 166 is disposed at proximal section 132 of inner tube 120. Accordingly, second coupling mechanism 166 is housed and/or retained within injection sheath 130 when injection sheath 130 is coupled to inner tube 120.

Figure 5:
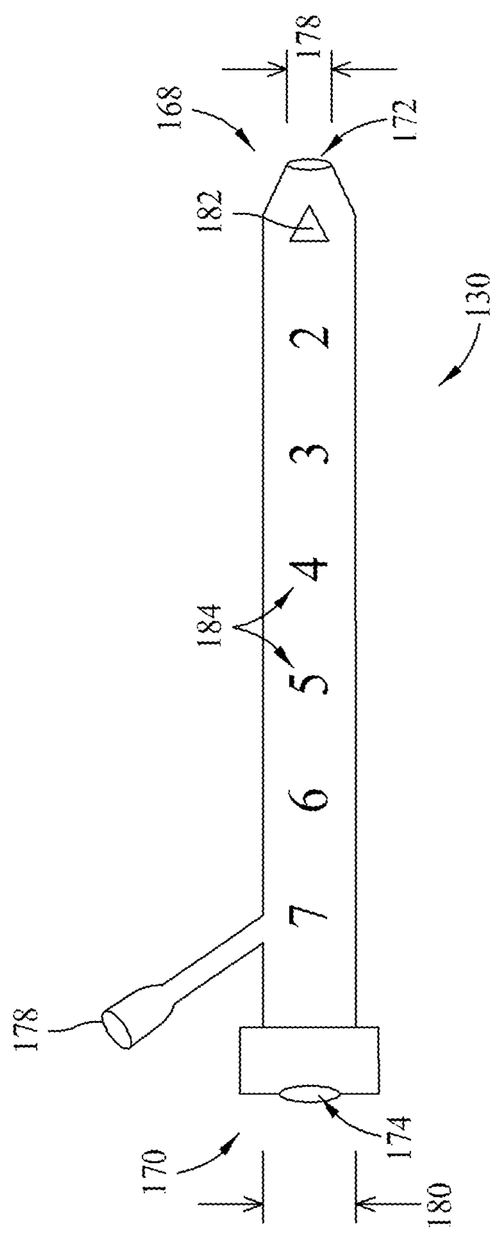
FIG. 5 is a perspective view of an exemplary injection sheath that may be used with the hemostatic system shown in FIG. 1.

FIG. 5 is a perspective view of injection sheath 130. In the exemplary embodiment, injection sheath 130 is coupled to inner tube 120 such that a distal end 168 of injection sheath 130 is positionable substantially adjacent artery 104. More specifically, when side opening 162 of inner tube 120 is positioned within artery 104, distal end 168 is positionable substantially adjacent, and outside, artery 104. In the exemplary embodiment, distal end 168 is tapered to facilitate traversing injection sheath 130 under skin surface 108 through subcutaneous tissue 106.

In the exemplary embodiment, injection sheath 130 is sized to house and/or retain approximately 4 milliliters (ml) of hemocoagulant agent in addition to proximal section 132 of inner tube 120, as described above. Alternatively, injection sheath 130 may have any size, shape, and/or configuration that enables hemostatic system 100 to function as described herein. In at least some embodiments, injection sheath 130 includes a retaining mechanism including, without limitation, a cap that is positionable at a proximal end 170 of injection sheath 130 to facilitate retaining the hemocoagulant agent within injection sheath 130. In one embodiment, the hemocoagulant agent is any FDA-approved powdered hemocoagulant agent commercially available. Alternatively, the hemocoagulant agent may be any substance and/or composition that enables injection sheath 130 to function as described herein.

In the exemplary embodiment, injection sheath 130 includes a distal end opening 172, a proximal end opening 174 through the proximal end cap, and a second lumen 176 (shown in FIG. 2) defined therebetween. In the exemplary embodiment, distal end opening 172 has a diameter, and proximal end opening 174 has a diameter that is different from distal end opening. More specifically, in the exemplary embodiment, distal end opening 172 has a diameter substantially equal to an outer diameter of inner tube 120, and proximal end opening 174 has a diameter substantially equal to an outer diameter of injection device 140. In the exemplary embodiment, injection sheath 130 has an inner diameter 180 that is larger than outer diameter of inner tube 120 in order to retain and/or channel the hemocoagulant agent through second lumen 176 about inner tube 120. Alternatively, inner diameter 180 may be any size, shape, and/or configuration that enables injection sheath 130 to function as described herein.

In the exemplary embodiment, injection sheath 130 includes at least one side opening 182 that is in fluid communication with second lumen 176. For example, in the exemplary embodiment, injection sheath 130 includes a plurality of side openings 182 spaced circumferentially about injection sheath 130. In the exemplary embodiment, side openings 182 are disposed less than approximately 20 millimeters (mm) (0.79 in.) from distal end opening 172. More particularly, in the exemplary embodiment, side openings 182 are disposed between approximately 5 mm (0.20 in.) and approximately 10 mm (0.39 in.) from distal end opening 172. Alternatively, injection sheath 130 may include any number of side openings 182 disposed in any location that enables hemostatic system 100 to function as described herein.

In the exemplary embodiment, injection sheath 130 includes a depth indicator 184 disposed along an outer surface of injection sheath 130. In the exemplary embodiment, depth indicator 184 is configured to provide and/or present to a user a distance side opening 162 and/or 182 is under skin surface 108. In the exemplary embodiment, depth indicator 184 includes a plurality of markings that are spaced evenly along the outer surface of injection sheath 130. More particularly, in the exemplary embodiment, the markings are spaced approximately 1 cm (0.39 in.) apart. Alternatively, depth indicator 184 may be any mechanism and/or device that enables injection sheath 130 to function as described herein.

In the exemplary embodiment, injection sheath 130 includes a side port 178 that communicates with second lumen 176. In the exemplary embodiment, side port 178 is positioned approximately 1.5 cm distal to cap 170 at proximal end of injection sheath 130. In the exemplary embodiment, side port 178 enables a hemocoagulant agent to be loaded into second lumen 176. Alternatively, side port 178 may be any size, shape, and/or configuration that enables the hemocoagulant agent to be loaded into second lumen 176.

Figure 6:
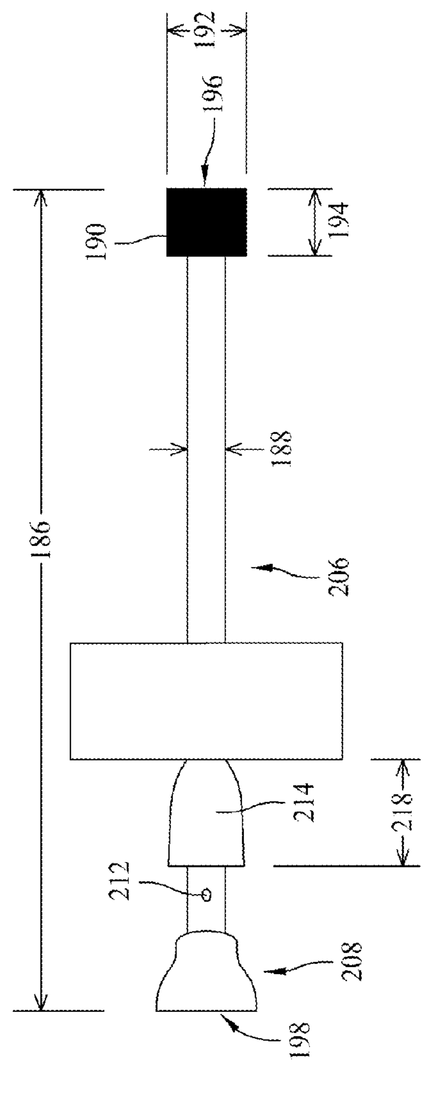
FIG. 6 is a perspective view of an exemplary outer tube that may be used with the hemostatic system shown in FIG. 1.
Figure 7:
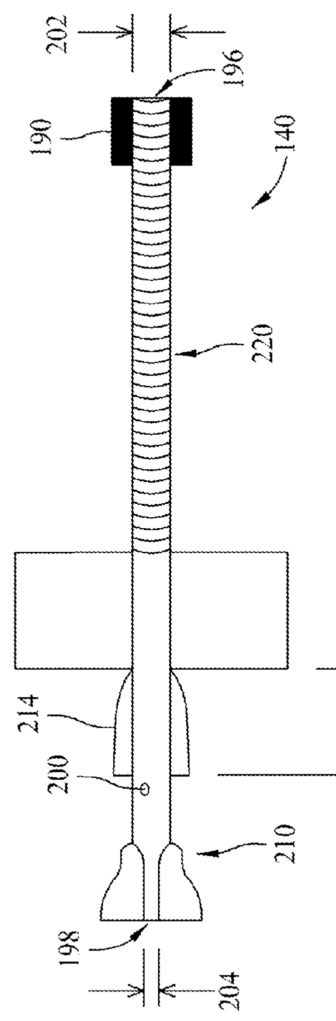
FIG. 7 is a cross-sectional view of the outer tube shown in FIG. 6.

FIG. 6 is a perspective view of injection device 140. FIG. 7 is a cross-sectional view of injection device 140. In the exemplary embodiment, injection device 140 has a length 186 of at least approximately 5 cm (1.97 in.). More particularly, in the exemplary embodiment, length 186 is between approximately 10 cm (3.94 in.) and approximately 15 cm (5.91 in.). In the exemplary embodiment, injection device 140 has an outer diameter 188 that is smaller than inner diameter 180 of injection sheath 130 such that injection device 140 may be positioned within injection sheath 130. Alternatively, injection device 140 may have any size, shape, and/or configuration that enables hemostatic system 100 to function as described herein.

In the exemplary embodiment, injection device 140 includes a plunger 190 that facilitates channeling the hemocoagulant agent through second lumen 176. In the exemplary embodiment, plunger 190 has an outer diameter 192 that is substantially similar to inner diameter 180 of injection sheath 130. In the exemplary embodiment, plunger 190 has a length 194 of at least approximately 1 cm (0.39 in.). Alternatively, plunger 190 may have any size, shape, and/or configuration that enables injection device 140 to function as described herein.

In the exemplary embodiment, injection device 140 includes a distal end opening 196, a proximal end opening 198, and a third lumen 200 defined therebetween. In the exemplary embodiment, distal end opening 196 has a first inner diameter 202 (shown in FIG. 7), and proximal end opening 198 has a second inner diameter 204 (shown in FIG. 7) that is different from first inner diameter 202. More specifically, in the exemplary embodiment, first inner diameter 202 is substantially equal to the outer diameter of inner tube 120, and second inner diameter 204 is substantially equal to the outer diameter of guidewire 102. For example, in the exemplary embodiment, second inner diameter 204 is approximately 0.035 in. to receive a 0.035 in. guidewire. Alternatively, inner diameters 202 and/or 204 may be any size, shape, and/or configuration that enables injection device 140 to function as described herein.

Accordingly, in the exemplary embodiment, third lumen 200 includes a first portion 206 corresponding to first inner diameter 202, and a second portion 208 corresponding to second inner diameter 204. More specifically, in the exemplary embodiment, first portion 206 extends between distal end opening 196 and a location 210 (shown in FIG. 7) approximately 1 cm (0.39 in.) from proximal end opening 198, and second portion 208 extends between proximal end opening 198 and location 210. Alternatively, portions 206 and/or 208 may have any size, shape, and/or configuration that enables injection device 140 to function as described herein.

In the exemplary embodiment, injection device 140 includes a side opening 212 in fluid communication with third lumen 200. In the exemplary embodiment, side opening 212 is disposed approximately 2 cm (0.79 in.) from proximal end opening 198. More specifically, in the exemplary embodiment, side opening 212 is in fluid communication with first portion 206 of third lumen 200. Alternatively, side opening 212 may be disposed in any location that enables injection device 140 to function as described herein.

In the exemplary embodiment, injection device 140 includes a valve 214 that is moveable to selectively restrict access to a portion of injection device 140. More specifically, in the exemplary embodiment, valve 214 is moveable between an open position and a closed position to selectively restrict access to side opening 212. In the open position, side opening 212 is at least partially exposed such that the fluid may flow into and/or out of third lumen 200 through side opening 212. Conversely, in the closed position, side opening 212 is substantially covered by valve 214 such that the fluid is restricted from flowing into and/or out of third lumen 200 through side opening 212.

In the exemplary embodiment, valve 214 is a sleeve that has an inner diameter larger than outer diameter 188 of injection device 140 such that valve 214 is slidable longitudinally along injection device 140. In the exemplary embodiment, valve 214 has a length 218 of at least approximately 1 cm (0.39 in.). Alternatively, valve 214 may have any size, shape, and/or configuration that enables injection device 140 to function as described herein.

In the exemplary embodiment, injection device 140 is removably coupleable to inner tube 120. More specifically, in the exemplary embodiment, injection device 140 includes a coupling mechanism 220 that is substantially complementary to second coupling mechanism 166 of inner tube 120. For example, in the exemplary embodiment, coupling mechanism 220 (shown in FIG. 7) is a plurality of threads that are configured to engage an outer surface of inner tube 120 in a threaded configuration. That is, in the exemplary embodiment, proximal section 132 of inner tube 120 has a threaded outer surface, and injection device 140 has a threaded inner surface that is substantially complementary to the threaded outer surface of inner tube 120. Accordingly, in the exemplary embodiment, injection device 140 is advanced longitudinally along inner tube 120 and/or through injection sheath 130 when injection device 140 is rotated about a longitudinal axis of injection device 140 in a clockwise or first direction. Conversely, in the exemplary embodiment, injection device 140 is withdrawn longitudinally along inner tube 120 and/or from injection sheath 130 when injection device 140 is rotated about the longitudinal axis of injection device 140 in a counterclockwise or second direction. In at least some embodiments, injection device 140 includes a handle that facilitates increasing a rotating efficiency of injection device 140. Alternatively, injection device 140 may be advanced and/or withdrawn using any mechanism and/or device that enables hemostatic system 100 to function as described herein.

When injection device 140 is coupled to inner tube 120, in the exemplary embodiment, third lumen 200 is in fluid communication with first lumen 150. Accordingly, in the exemplary embodiment, the fluid enters locator device 110 through side opening 162 of inner tube 120, is channeled through lumens 150 and 200, and is discharged from side opening 212 of injection device 140.

Figure 8:
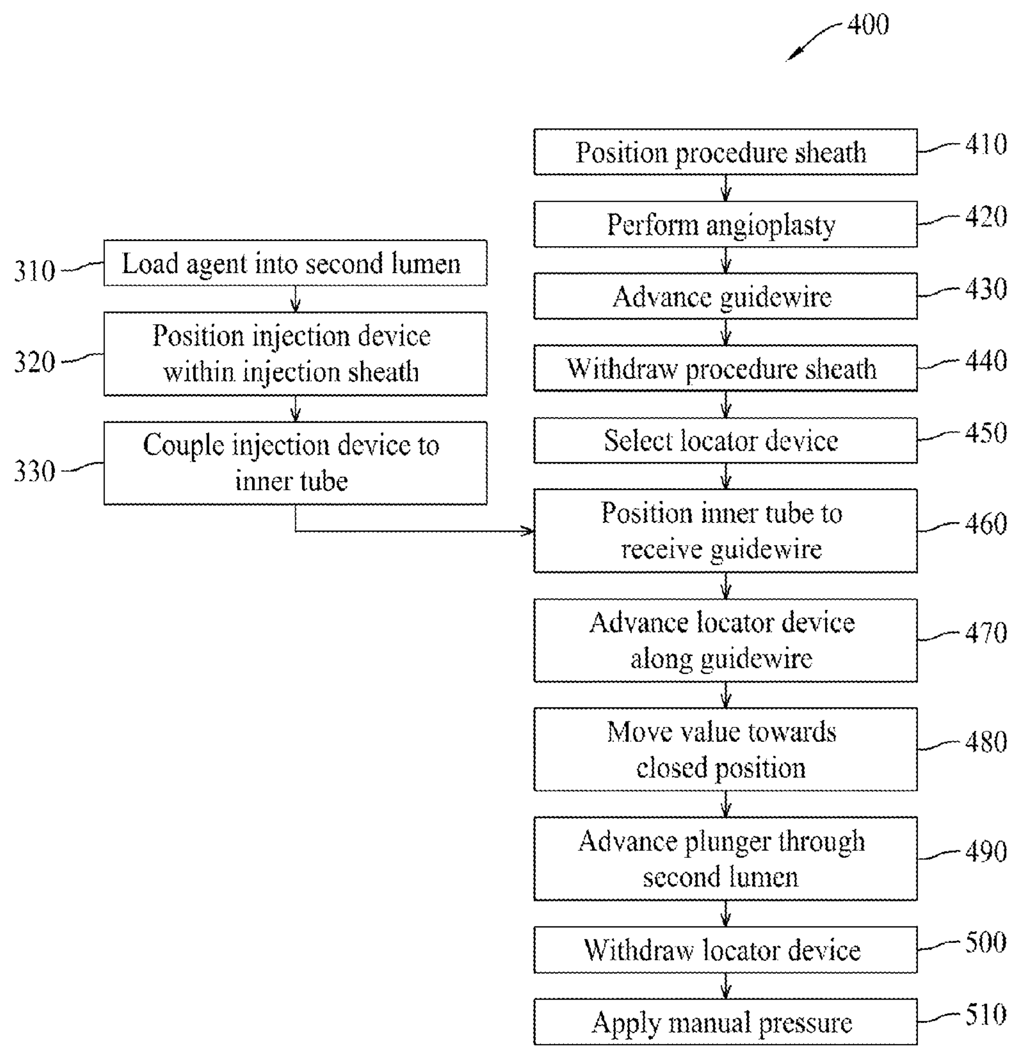
FIG. 8 is a flow chart illustrating an exemplary method of using the hemostatic system shown in FIG. 1.

FIG. 8 is a flow chart illustrating an exemplary method 300 of using hemostatic system 100 to seal a puncture of artery 104 with a powdered hemocoagulant agent. In the exemplary embodiment, first coupling mechanism 164 couples injection sheath 130 to inner tube 120. To prepare hemostatic system 100 for use, in the exemplary embodiment, the powdered hemocoagulant agent is loaded 310 into second lumen 176 between an inner surface of injection sheath 130 and an outer surface of inner tube 120 through side port 178 of injection sheath 130. In the exemplary embodiment, at least a portion of injection device 140 is positioned 320 within injection sheath 130. More specifically, in the exemplary embodiment, a distal end of injection device 140 is advanced through proximal end opening 174 of injection sheath 130 such that at least the distal end of injection device 140 is positioned 320 within injection sheath 130. In the exemplary embodiment, injection device 140 is coupled 330 to inner tube 120 within injection sheath 130. More specifically, in the exemplary embodiment, coupling mechanisms 166 and/or 220 enable an inner surface of injection device 140 to engage an outer surface of inner tube 120.

During operation, in the exemplary embodiment, a procedure sheath (not shown) used during a medical procedure is positioned 410 such that a tip of the procedure sheath is approximately 10 cm (3.94 in.) from the access site and is substantially free of at least some devices. Alternatively, the tip of the procedure sheath may be positioned in any location that enables hemostatic system 100 to function as described herein. In the exemplary embodiment, a limited angiography is performed 420 through the procedure sheath to assess the puncture of artery 104 and/or to ensure that the procedure sheath is positioned within artery 104.

In the exemplary embodiment, guidewire 102 is advanced 430 through the procedure sheath to artery 104 such that a tip of guidewire 102 is positioned at least approximately 5 cm (1.97 in.) beyond the tip of the procedure sheath. More particularly, the tip of guidewire 102 is positioned approximately 10 cm (3.94 in.) beyond the tip of the procedure sheath. Alternatively, the tip of guidewire 102 may be positioned in any location that enables hemostatic system 100 to function as described herein.

In the exemplary embodiment, the procedure sheath is withdrawn 440 from the access site longitudinally along guidewire 102 while manual pressure is applied over the access site. Hemostatic system 100 is selected 450 based on a size of the procedure sheath and/or the access site. For example, in this exemplary embodiment, hemostatic system 100 is selected 450 to include an inner tube 120 having an outer diameter that is generally the same as an outer diameter of the procedure sheath and/or the access site. Alternatively, hemostatic system 100 may be selected based on any criteria and/or factor that enables hemostatic system 100 to function as described herein.

In the exemplary embodiment, inner tube 120 is aligned and/or positioned 460 to receive guidewire 102. More specifically, guidewire 102 is inserted through distal end opening 146 of inner tube 120, and hemostatic system 100 is advanced 470 longitudinally along guidewire 102 with inner tube 120 advanced through arteriortomy site into the lumen of artery 104. Hemostatic system 100 is advanced 470 until a fluid refluxes and/or is discharged from side opening 212 of injection device 140. In this exemplary embodiment, the fluid discharge indicates that side opening 162 of inner tube 120 is positioned within artery 104 and/or side openings 182 of injection sheath 130 are positioned outside artery 104. Valve 214 is moved 480 towards the closed position to restrict access to side opening 212 and facilitate retaining the fluid within artery 104, first lumen 150, and/or third lumen 200.

In the exemplary embodiment, plunger 190 is advanced 490 through second lumen 176 to channel the powdered hemocoagulant agent through second lumen 176. More specifically, injection device 140 is rotated about the longitudinal axis of injection device 140 in a clockwise or first direction to advance plunger 190 and discharge the powdered hemocoagulant agent from side openings 182 of injection sheath 130. In at least some embodiments, a depth is indicated on depth indicator 184, and hemostatic system 100 is maintained at the identified depth. In the exemplary embodiment, the injection process may be repeated as hemostatic system 100 is withdrawn 500 from subcutaneous tissue 106. In at least some embodiments, the repeated injection process may include systematically withdrawing 500 hemostatic system 100 from subcutaneous tissue 106 based on the depth indicated on depth indicator 184. In the exemplary embodiment, direct, non-occlusive manual pressure is continuously applied 510 to the access site after hemostatic system 100 is withdrawn from subcutaneous tissue 106 until hemostasis is achieved.

The methods and apparatus described herein relate to medical devices and, more particularly, to a hemostatic system. The hemostatic system described herein facilitates sealing, for example, an arterial opening. The exemplary hemostatic system includes at least an injection sheath and an injection device. The injection device is advanced through the injection sheath to inject a powdered hemocoagulant agent at and/or around the arterial opening. The powdered hemocoagulant agent facilitates sealing the arterial opening to reduce a time required for hemostasis and/or ambulation.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A hemostatic system for sealing a puncture of a vessel, said hemostatic system comprising:

an inner tube comprising an inner tube distal end opening, an inner tube proximal end opening, and an inner tube side opening, said inner tube defines a first lumen extending between said inner tube distal end opening and said inner tube proximal end opening, said inner tube is configured to receive a guidewire through said inner tube distal end opening, said first lumen, and said inner tube proximal end opening, wherein a diameter of a distal portion of said first lumen is substantially equal to a diameter of the guidewire;

an injection sheath coupled to said inner tube, said injection sheath housing at least a section of said inner tube, said injection sheath defines a second lumen configured to channel a hemocoagulant agent therethrough; and an injection device positionable within said injection sheath to facilitate channeling the hemocoagulant agent through said second lumen, said injection device comprising an injection device distal end opening, an injection device proximal end opening, and an injection device side opening, said injection device defining a third lumen extending between said injection device distal end opening and said injection device proximal end opening, said injection device is configured to receive the guidewire through said injection device distal end opening, said third lumen, and said injection device proximal end opening, said injection device further comprising:

a plunger; and a distal section threadably coupled to said inner tube, such that said plunger is advanceable through said second lumen via rotation of said injection device relative to said inner tube to facilitate channeling the hemocoagulant agent through said second lumen, wherein said inner tube side opening, said first lumen, said third lumen, and said injection device side opening are coupled in fluid communication.

2. A hemostatic system in accordance with claim 1, wherein a diameter of a proximal portion of said inner tube lumen is sized to channel a fluid about the guidewire received therethrough.

3. A hemostatic system in accordance with claim 1, wherein said injection device comprises a first section having a first inner diameter and a second section having a second inner diameter that is different from the first inner diameter.

4. A hemostatic system in accordance with claim 1, wherein said plunger comprises an outer diameter that is substantially similar to an inner diameter of said injection sheath.

5. A hemostatic system in accordance with claim 1, wherein said injection sheath comprises a length indicator.

6. A hemostatic system in accordance with claim 1, wherein said injection device further comprises a valve that is moveable to selectively control a first fluid flow through said inner tube side opening, said first lumen, said third lumen, and said injection device side opening.

7. A hemostatic system for sealing a puncture of a vessel, said hemostatic system comprising:

an inner tube comprising an inner tube distal end opening, an inner tube proximal end opening, and an inner tube side opening, said inner tube defines an inner tube lumen extending between said inner tube distal end opening and said inner tube proximal end opening;

an outer tube removably coupled to said inner tube, said outer tube comprising a plunger, an outer tube distal end opening, an outer tube proximal end opening, and an outer tube side opening, said outer tube defines an outer tube lumen extending between said outer tube distal end opening and said outer tube proximal end opening, said outer tube comprising a valve that is slidable along a length of said outer tube to selectively enable and restrict emission of a first fluid flow out of said outer tube side opening from a channel defined by said inner tube side opening, said inner tube lumen, said outer tube lumen, and said outer tube side opening; and an injection sheath sized to house at least a section of said inner tube, said injection sheath defining an injection sheath lumen, wherein said plunger is advanceable through said injection sheath lumen to facilitate channeling a hemocoagulant agent therethrough.

8. A hemostatic system in accordance with claim 7, wherein said inner tube comprises a coupling mechanism configured to couple said inner tube to said injection sheath.

9. A hemostatic system in accordance with claim 7, wherein said inner tube comprises a first section having a threaded outer surface, and said outer tube comprises a second section having a threaded inner surface that is substantially complementary to said threaded outer surface.

10. A hemostatic system in accordance with claim 7, wherein said inner tube comprises a first section having a first inner diameter and a second section having a second inner diameter that is different from the first inner diameter.

11. A hemostatic system in accordance with claim 7, wherein said outer tube comprises a first section having a first inner diameter and a second section having a second inner diameter that is different from the first inner diameter.

12. A hemostatic system in accordance with claim 7, wherein said plunger comprises an outer diameter that is substantially similar to an inner diameter of said injection sheath.

13. A hemostatic system in accordance with claim 7, wherein said injection sheath comprises a length indicator.

14. A hemostatic system in accordance with claim 7, wherein said hemostatic system is configured to receive a guidewire through said inner tube distal end opening, said inner tube lumen, said outer tube lumen, and said outer tube proximal opening.

15. A hemostatic system for sealing a puncture of a vessel, said hemostatic system comprising:

an inner tube comprising an inner tube distal end opening, an inner tube proximal end opening, and an inner tube side opening, said inner tube defines an inner tube lumen extending between said inner tube distal end opening and said inner tube proximal end opening;

an outer tube comprising a plunger, an outer tube distal end opening, an outer tube proximal end opening, and an outer tube side opening, said outer tube defines an outer tube lumen extending between said outer tube distal end opening and said outer tube proximal end opening, said outer tube threadably coupled to said inner tube, wherein said inner tube lumen and said outer tube lumen cooperate to define a closed flow path for a first fluid flow between said inner tube side opening and said outer tube side opening; and an injection sheath sized to house at least a section of said inner tube, said injection sheath defining an injection sheath lumen, wherein said plunger is advanceable through said injection sheath lumen via threaded rotation of said outer tube relative to said inner tube to facilitate channeling a hemocoagulant agent through said injection sheath lumen.

16. A hemostatic system in accordance with claim 15, wherein said inner tube comprises a first section having a first inner diameter and a second section having a second inner diameter that is different from the first inner diameter.

17. A hemostatic system in accordance with claim 15, wherein said outer tube comprises a first section having a first inner diameter and a second section having a second inner diameter that is different from the first inner diameter.

18. A hemostatic system in accordance with claim 15, wherein said plunger comprises an outer diameter that is substantially similar to an inner diameter of said injection sheath.

* * * * *